(12) United States Patent
O'Connor et al.

(10) Patent No.: US 12,178,438 B2
(45) Date of Patent: *Dec. 31, 2024

(54) DEPLOYING EMBOLIC COILS

(71) Applicant: Boston Scientific Scimed Inc., Maple Grove, MN (US)

(72) Inventors: Aidan O'Connor, Carrigtohill (IE); Christopher J. Elliott, Hopkinton, MA (US); Mary McCarthy, Cork (IE); Ines Burgos, Worcester, MA (US); Marcia S. Buiser, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 152 days.

This patent is subject to a terminal disclaimer.

(21) Appl. No.: 17/895,269

(22) Filed: Aug. 25, 2022

(65) Prior Publication Data

US 2023/0024166 A1 Jan. 26, 2023

Related U.S. Application Data

(63) Continuation of application No. 16/703,993, filed on Dec. 5, 2019, now Pat. No. 11,446,038, which is a continuation of application No. 12/029,990, filed on Feb. 12, 2008, now Pat. No. 10,524,799.

(60) Provisional application No. 60/905,023, filed on Mar. 5, 2007.

(51) Int. Cl.
*A61M 25/00* (2006.01)
*A61B 17/12* (2006.01)
*A61M 29/00* (2006.01)

(52) U.S. Cl.
CPC .. *A61B 17/12022* (2013.01); *A61B 17/12113* (2013.01); *A61B 17/12145* (2013.01); *A61B 17/1215* (2013.01); *A61B 2017/12054* (2013.01)

(58) Field of Classification Search
CPC ........ A61B 17/12022; A61B 17/12113; A61B 17/12145; A61B 17/12154; A61B 17/1214; A61B 17/12131
See application file for complete search history.

(56) References Cited

U.S. PATENT DOCUMENTS

| | | |
|---|---|---|
| 4,897,255 A | 1/1990 | Fritzberg et al. |
| 5,226,911 A | 7/1993 | Chee et al. |
| 5,304,195 A | 4/1994 | Twyford, Jr. et al. |
| 5,382,260 A | 1/1995 | Dormandy, Jr. et al. |
| 5,423,849 A | 6/1995 | Engelson et al. |
| 5,573,547 A | 11/1996 | LeVeen et al. |
| 5,639,277 A | 6/1997 | Mariant et al. |
| 5,645,558 A | 7/1997 | Horton |

(Continued)

FOREIGN PATENT DOCUMENTS

| | | |
|---|---|---|
| EP | 0913124 A2 | 5/1995 |
| WO | 2005113035 A2 | 12/2005 |
| WO | 2008109228 A2 | 9/2008 |

*Primary Examiner* — Tuan V Nguyen
(74) *Attorney, Agent, or Firm* — Seager, Tufte & Wickhem, LLP

(57) ABSTRACT

An embolic coil delivery system includes a catheter and an embolic coil disposed within the catheter, the embolic coil including a coil wire and a fiber bundle. A method of producing an embolic coil delivery system includes: advancing a delivery sheath over a distal end of an embolic coil while applying tension to the embolic coil via a retaining device that is attached to the distal end of the embolic coil.

20 Claims, 13 Drawing Sheets

(56) References Cited

U.S. PATENT DOCUMENTS

| | | |
|---|---|---|
| 5,658,308 A | 8/1997 | Snyder |
| 5,700,258 A | 12/1997 | Mirigian et al. |
| 5,718,711 A | 2/1998 | Berenstein et al. |
| 5,733,925 A | 3/1998 | Kunz et al. |
| 5,797,953 A | 8/1998 | Tekulve |
| 5,830,230 A | 11/1998 | Berryman et al. |
| 5,833,705 A | 11/1998 | Ken et al. |
| 5,895,385 A | 4/1999 | Guglielmi et al. |
| 5,935,145 A | 8/1999 | Villar et al. |
| 5,976,162 A | 11/1999 | Doan et al. |
| 6,001,092 A | 12/1999 | Mirigian et al. |
| 6,024,765 A | 2/2000 | Wallace et al. |
| 6,117,157 A | 9/2000 | Tekulve |
| 6,126,672 A | 10/2000 | Berryman et al. |
| 6,136,015 A | 10/2000 | Kurz et al. |
| 6,143,007 A | 11/2000 | Mariant et al. |
| 6,190,373 B1 | 2/2001 | Palermo et al. |
| 6,193,728 B1 | 2/2001 | Ken et al. |
| 6,368,658 B1 | 4/2002 | Schwarz et al. |
| 6,494,884 B2 | 12/2002 | Gifford et al. |
| 6,511,468 B1 | 1/2003 | Cragg et al. |
| 6,545,097 B2 | 4/2003 | Pinchuk et al. |
| 6,660,020 B2 | 12/2003 | Wallace et al. |
| 7,247,159 B2 | 7/2007 | Lorenzo et al. |
| 7,857,825 B2 | 12/2010 | Moran et al. |
| 8,101,197 B2 | 1/2012 | Buiser et al. |
| 8,152,839 B2 | 4/2012 | Buiser et al. |
| 2002/0151926 A1 | 10/2002 | Wallace et al. |
| 2003/0093111 A1 | 5/2003 | Ken et al. |
| 2004/0059371 A1 | 3/2004 | Healy et al. |
| 2004/0076582 A1 | 4/2004 | DiMatteo et al. |
| 2004/0186491 A1* | 9/2004 | Klint ............... A61B 17/12172 606/158 |
| 2005/0004598 A1 | 1/2005 | White et al. |
| 2005/0228435 A1 | 10/2005 | Lorenzo et al. |
| 2005/0245963 A1 | 11/2005 | Kida et al. |
| 2006/0036281 A1 | 2/2006 | Patterson et al. |
| 2006/0116711 A1 | 6/2006 | Elliott et al. |
| 2006/0276827 A1 | 12/2006 | Mitelberg et al. |
| 2007/0141099 A1 | 6/2007 | Buiser et al. |
| 2007/0142859 A1 | 6/2007 | Buiser et al. |
| 2007/0142893 A1 | 6/2007 | Buiser et al. |

\* cited by examiner

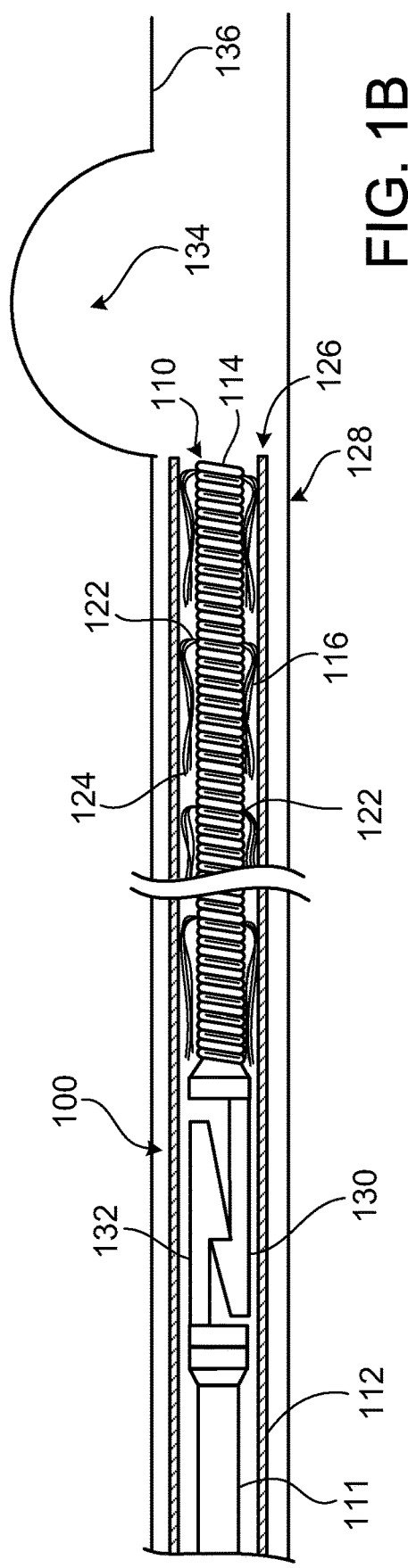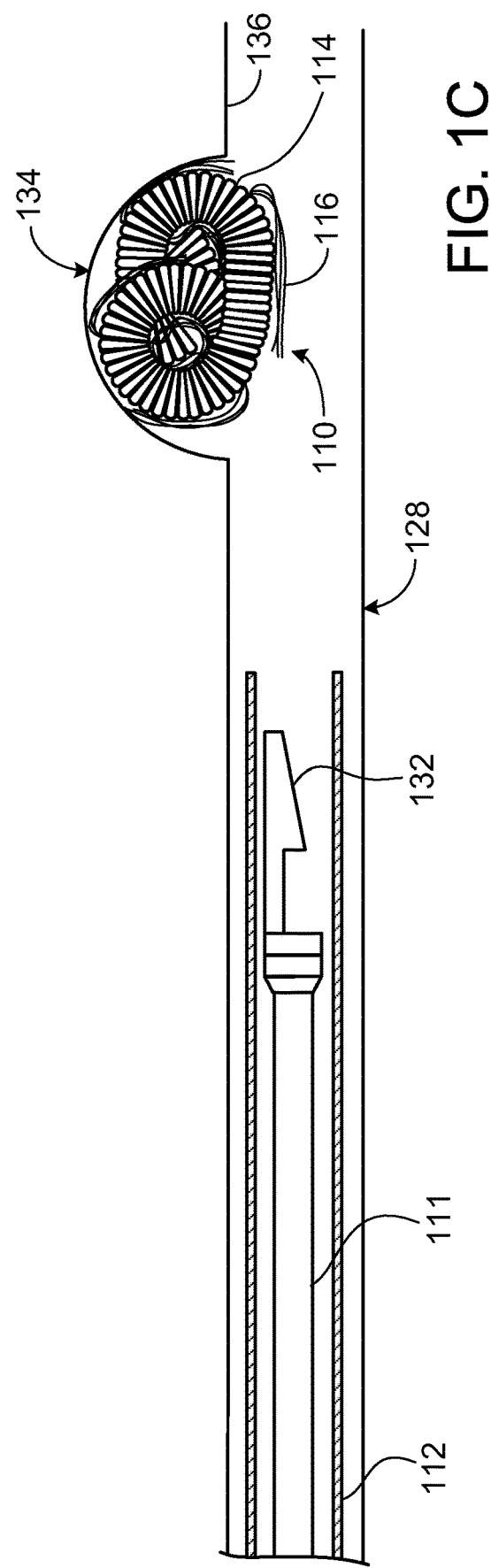

DEPLOYING EMBOLIC COILS

CROSS-REFERENCE TO RELATED APPLICATIONS

This application is a continuation of U.S. application Ser. No. 16/703,993, filed Dec. 5, 2019, which is a continuation of U.S. application Ser. No. 12/029,990, filed Dec. 12, 2008, which claims priority under 35 USC § 119(e) U.S. Provisional patent application Ser. No. 60/905,023, filed Mar. 5, 2007, the entire contents of which are hereby incorporated by reference.

TECHNICAL FIELD

The disclosure relates to embolic coils, as well as related methods and devices.

BACKGROUND

Therapeutic vascular occlusions (embolizations) are used to prevent or treat pathological conditions in situ. Embolic coils can be used to occlude vessles in a variety of medical applications. Delivery of embolic coils (e.g., through a catheter) can depend on the size and/or shape of the coils. Some embolic coils include fibers that can, for example, enhance thrombosis at the treatment site.

SUMMARY

In some systems, fibered coils can be placed in delivery catheters with fiber bundles oriented to facilitate delivery of the coil out of the catheter. In some coils, the distribution of the fiber bundles along the coils varies such that fiber bundle density, and thus column strength, is higher near the point at which deployment force is applied to the coil.

In one aspect, a system includes a catheter having a delivery end; and an embolic coil at least partially disposed within the catheter. The embolic coil includes a coil wires having an end fitting configured to releasably couple to an end fitting of a delivery wire, and a fiber bundle contacting the catheter, the fiber bundle having a first bundle end being attached to the coil wire and a second bundle end opposite the first bundle end. The fiber bundle is disposed such that a distance from the first bundle end to the delivery end of the catheter is less than a distance from the second bundle end to the delivery end of the catheter.

In some embodiments, the embolic coil comprises multiple fiber bundles contacting the catheter, each fiber bundle having first and second bundle ends, the first bundle end being attached to the coil wire, the second bundle end opposite the first bundle end, the fiber bundle being disposed such that a distance from the first bundle end of a specific fiber bundle to the delivery end of the catheter is less than a distance from the second bundle end of the specific fiber bundle to the delivery end of the catheter. In some cases, more fiber bundles are attached to a first half of the coil than are attached to a second half of the coil.

In some embodiments, the coil is disposed in the catheter such that the second half of the coil is between the first half of the coil and the delivery end of the catheter.

In some embodiments, spacing between adjacent fiber bundles increases with increasing distance from the end fitting of the coil wire.

In some embodiments, the fiber bundles are disposed in at least one group and the spacing between adjacent fiber bundles is constant within each group of the at least one group.

In some embodiments, each fiber bundle is attached to the coil wire at an attachment point and a first attachment point is circumferentially spaced apart from a second attachment point. In some cases, the attachment point of each fiber bundle is circumferentially spaced apart from the attachment points of adjacent fiber bundles.

In some embodiments, the fiber bundle comprises polyethylene terephthalate or nylon.

In some embodiments, wherein the coil wire has a diameter from 0.0075 inch to 0.015 inch.

In some embodiments, wherein the fiber bundle has a length from 0.025 inch to 0.125 inch.

In some embodiments, the coil wire comprises a metal.

In some embodiments, the system also includes a lubricant disposed within the catheter. In some cases, the lubricant is disposed on the fiber bundle.

In some embodiments, an inner surface of the catheter includes a material selected from the group consisting of polypropylene, polytetrafluoroethylene (PTFE), fluoroethylene polymer (FEP), low-density polyethylene (LDPE), high-density polyethylene (HDPE), nylon, Teflon®, and acrylic.

In one aspect, a coil includes: a coil wire having a first end, and opposite second end, and a midpoint located halfway between the first end and the second end; and multiple fiber bundles attached to the coil wire. More fiber bundles are attached to the coil wire between the first end and the midpoint than are attached to the coil wire between the second end and the midpoint. The coil is an embolic coil.

In some embodiments, spacing between adjacent fiber bundles increases with increasing distance from the first end of the coil.

In some embodiments, the fiber bundles are disposed in at least one group and the spacing between adjacent fiber bundles is constant within each group of the at least one group.

In some embodiments, the coil also includes a end fitting attached to the first end of the coil wire, the end fitting configured to releasably couple the embolic coil to a mating end fitting of a delivery wire.

In some embodiments, a proximal end of the coil wire is configured to provide an opposable surface configured for engagement of a pusher element.

In one aspect, a system includes: a catheter having a delivery end; a delivery wire with an end fitting; and an embolic coil disposed within the catheter, the embolic coil having a first half and a second half, the second half disposed between the first half and the delivery end of the catheter, the embolic coil including a coil wire and multiple fiber bundles contacting the catheter, the coil wire having an end fitting configured to releasably couple to the end fitting of the delivery wire and each fiber bundle extending from a first bundle end attached to the coil wire to a second bundle end opposite the first bundle end. A majority of the fiber bundles are angled such that a distance from the first bundle end of a specific fiber bundle to the delivery end of the catheter is less than a distance from the second bundle end of the specific fiber bundle to the delivery end of the catheter. More fiber bundles are attached to the first half of the embolic coil than are attached to a second half of the coil.

In some embodiments, spacing between adjacent fiber bundles increases with increasing distance from the end fitting of the coil wire.

In some embodiments, the fiber bundles are disposed in groups and the spacing between adjacent fiber bundles is constant within each group.

In some embodiments, each fiber bundle is attached to the coil wire at an attachment point and a first attachment point is circumferentially spaced apart from a second attachment point. In some cases, the attachment point of each fiber bundle is circumferentially spaced apart from the attachment points of adjacent fiber bundles.

In one aspect, a method includes: advancing a delivery sheath over a distal end of an embolic coil while applying tension to the embolic coil via a retaining device that is attached to the distal end of the embolic coil.

In some embodiments, the method also includes engaging fiber bundles extending from a first bundle end attached to the coil wire to a second bundle end with the sheath such that, for a majority of the fiber bundles, a distance from the first bundle end of a specific fiber bundle to a proximal end fitting of the embolic coil is greater than a distance from the second bundle end of the specific fiber bundle to the end fitting of the embolic coil. In some cases, the method also includes stopping advancement of the sheath after the distal end of the coil emerges from a delivery end of the sheath and before any of the fiber bundles emerge from the delivery end of the sheath. In some cases, the method also includes detaching the retaining device from the distal end of the coil. In some cases, the method also includes refining the distal end of the coil. In some cases, the method also includes withdrawing the distal end of the coil into the sheath.

In some embodiments, the method also includes stopping advancement of the catheter over the embolic coil before a proximal end of the coil enters the sheath. In some cases, the method also includes engaging an end fitting of a delivery wire with a proximal end fitting of the coil.

In some embodiments, the coils can exhibit relatively little friction during deployment.

In certain embodiments, the coils exhibit relatively high column strength near the point of application of deployment force at the proximal end of the coil.

Other features and advantages will be apparent from the description, drawings, and claims.

DESCRIPTION OF DRAWINGS

FIGS. 1A-1C are a cross-sectional views of an embodiment of an embolic coil delivery system before, during, and after delivery of an embolic coil.

Like reference symbols in the various drawings indicate like elements.

DETAILED DESCRIPTION

Embolic coils can be used for purposes including, for example, to close blood vessels and/or fill aneurysmal sacs. Fibered embolic coils can include thrombogenic fiber bundles attached to the coil at prescribed intervals to enhance coil thrombosis. Detachable coils include a pre-attached delivery system (typically a wire) for delivery of the coil to the desired site. Upon completion of satisfactory positioning, the embolic coil is detached from the delivery system. Pushable coils are not attached to the delivery system but rather are pushed by wire-like devices for one-way deployment.

Figure 1A:
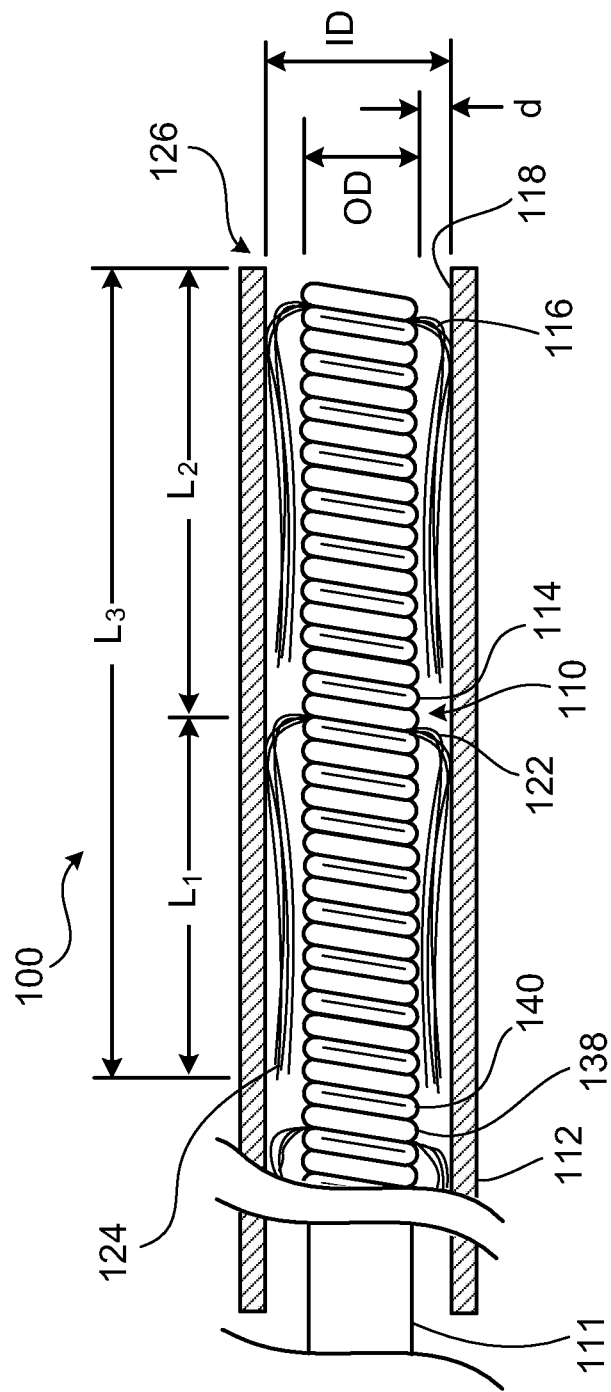

FIGS. 1A-1C show the use of an embolic coil delivery system 100 to deliver a detachable embolic coil 110 to fill and occlude an aneurysmal sac 134. Embolic coil delivery system 100 includes an embolic coil 110 disposed within a catheter 112. Embolic coil 110 is detachably engaged to delivery wire 111 which extends proximally out of catheter 112. In some embodiments, embolic coil 110 can be disposed within a carrier fluid (e.g., a saline solution, a contrast agent, a heparin solution) while embolic coil 110 is within catheter 112. In FIG. 1B, catheter 112 is delivered into a lumen 128 of a subject. An end fitting 130 of embolic coil 110 is detachably engaged with an end fitting 132 of delivery wire 111. The end fittings 130, 132 can be maintained in engagement with each other while coil 110 is in catheter 112 because there is insufficient clearance in catheter 112 for them to disengage. Delivery wire 111 is used to push embolic coil 110 out of catheter 112 through delivery end 126 of catheter 112, into lumen 128, and toward an aneurysmal sac 134 formed in wall 136 of lumen 128. FIG. 1C shows embolic coil 110 filling aneurysmal sac 134 after embolic coil 110 has been pushed out of catheter 112 and disengaged from delivery wire 111. By filling aneurysmal sac 134, embolic coil 110 helps to occlude aneurysmal sac 134. This occlusion of aneurysmal sac 134 can be accelerated by fiber bundles 116, which can enhance thrombosis within aneurysmal sac 134. An accelerated embolization procedure can benefit the subject by, for example, reducing exposure time to fluoroscopy.

Detachable embolic coils are described, for example, in Twyford, Jr. et al., U.S. Pat. No. 5,304,195; Guglielmi et al., U.S. Pat. No. 5,895,385; and Buiser et al., U.S. patent application Ser. No. 11/311,617, filed on Dec. 19, 2005, and entitled "Coils".

Embolic coil 110 includes a coil wire 114. In some embodiments, coil wire 114 is wound in a spiral configuration. Fiber bundles 116 extend from coil wire 114 into contact with inner surfaces 118 of catheter 112 such that the fibers in fiber bundles 116 are axially deflected. In general, fiber bundles 116 include multiple fibers extending from a single attachment point as shown. However, in some embodiments, a single fiber can make up a fiber bundle.

The fiber bundles 116 can have a length $L_1$ that exceeds a radial distance d between coil wire 114 and inner surfaces 118 of catheter 112. For example, one embodiment of an embolic coil delivery system includes an embolic coil wire portion with an outer diameter OD of 0.012 inch, a catheter with an inner diameter ID of 0.021 inch, and fiber bundles 116 with a length $L_1$ of 0.079 inch. As will be described in more detail below, embolic coil 110 is loaded into catheter 112 such that fiber bundles 116 extend from their point of attachment to coil wire 114 away from delivery end 126 of catheter 112. For example, in the embodiment shown in FIGS. 1A and 1B, a first end 122 of fiber bundle 116 is attached to coil wire 114. Fiber bundle 116 contacts inner surface 118 of catheter 112 and extends away from delivery end 126 of catheter 112 to second end 124 of fiber bundle 116 (e.g., a distance $L_2$ from first bundle end 122 to delivery end 126 of catheter 112 is less than a distance $L_3$ from second bundle end 124 to delivery end 126 of the catheter 112). In some embodiments, an inner surface 118 of catheter 112 comprises a material with a coefficient of friction below about 0.3 (e.g., polypropylene, polytetrafluoroethylene (PTFE), fluoroethylene polymer (FEP), low-density polyethylene (LDPE), high-density polyethylene (HDPE), nylon, Teflon®, acrylic).

In some cases, during delivery, thrombus can begin to build up on embolic coil 110 within catheter 112. The configuration of fiber bundles 116 as described above can reduce friction between embolic coil 110 and catheter 112 during deployment of embolic coil 110, which, in turn, can reduce the possibility that coil 110 will undesirably buckle during delivery.

Coil wire 114 includes windings 138 and 140. In general, there is little to no space between consecutive windings (e.g., windings 138 and 140) of embolic coil 110. As a result, fiber bundles 116 are generally tightly fitted between consecutive windings of embolic coil 110.

The pitch of an embolic coil is the sum of the thickness of one winding of coil wire 114 (e.g., winding 138) and the amount of space between that winding and a consecutive winding (e.g., winding 140). In some embodiments, embolic coil 110 can have a pitch of at most about 0.01 inch (e.g., about 0.003 inch). Because the windings of embolic coil 110 are flush with each other, the pitch of embolic coil 110 is equal to the diameter of coil wire 114.

The diameter of coil wire 114 can be selected, for example, based on the desired properties (e.g., size, strength) and/or applications of embolic coil 110. In some embodiments, coil wire 114 can have a diameter of from 0.001 inch to 0.005 inch (e.g., from 0.0015 inch to 0.005 inch, from 0.002 inch to 0.003 inch, from 0.00225 inch to 0.003 inch). In certain embodiments, coil wire 114 can have a diameter of 0.003 inch. In some embodiments (e.g., embodiments in which embolic coil 110 is used for peripheral vascular applications), coil wire 114 can have a diameter of at least about 0.004 inch. In certain embodiments (e.g., embodiments in which embolic coil 110 is used for neurological applications), coil wire 114 can have a diameter of at most about 0.002 inch. Alternatively or additionally, coil wire 114 can have a restrained length of at most about 50 centimeters (e.g., at most about 40 centimeters, at most about 30 centimeters, at most about 20 centimeters).

Coil wire 114 can be formed of, for example, one or more metals or metal alloys, such as platinum, a platinum alloy (e.g., a platinum-tungsten alloy), stainless steel, nitinol, and Elgiloy® (from Elgiloy Specialty Metals). Embolic coils can be formed from wires with a round cross-section (see FIGS. 1A-1C) or from wires with other cross sections (e.g., ribbon-shaped wires; see FIGS. 5A and 5B).

Fiber bundles 116 are typically formed of one or more materials that can enhance thrombosis (e.g., at a target site). Examples of materials from which fiber bundles 116 can be made include polyethylene terephthalate (e.g., Dacron®), nylon, and collagen. Fibers can be made from materials with a coefficient of friction below about 0.35. Fiber bundles 116 can have a length of from about 0.5 millimeter to about five millimeters (e.g., about 2.5 millimeters).

Embolic coils can generally be used in a number of different applications, such as neurological application and/or peripheral applications. In some embodiments, embolic coils can be used to occlude a vessel, and/or to treat an aneurysm (e.g., an intercranial aneurysm), an arteriovenous malformation (AVM), or a traumatic fistula. In some embodiments, embolic coils can be used to embolize a tumor (e.g., a liver tumor). In certain embodiments, embolic coils can be used in transarterial chemoembolization (TACE).

Fibered embolic coils can have fiber bundle distributions that are substantially uniform along the length of the coils (see FIGS. 1A-1C). However, fibered embolic coils can also have fiber bundle distributions that vary along the length of the coils such that the fiber density (e.g., fiber bundles per unit length of the coil) is greater in some portions of the coils that in other portions of the coils. For example, there can be more fiber bundles attached to a proximal half of the embolic coil than are attached to a distal half of embolic coil. In some instances, the distribution of fiber bundles in an embolic coil can affect the structural properties of the coil.

In some embodiments, the presence of fiber bundles can increase the column strength of a first section of an embolic coil where fiber bundles are present relative to a second section of the embolic coil where fewer (e.g., none) fiber bundles are present. For example, by locating the first section proximally of the second section, a proximal half of the embolic coil can include more fiber bundles than a distal half of the embolic coil. Increasing the fiber density of embolic coil near a proximal end of the embolic coil where a pusher wire contacts the embolic coil can concentrate sources of friction (e.g., fiber bundles and associated thrombus) near the location at which the delivery force is applied. In some cases, this can reduce the likelihood of a jammed coil.

Figure 2:
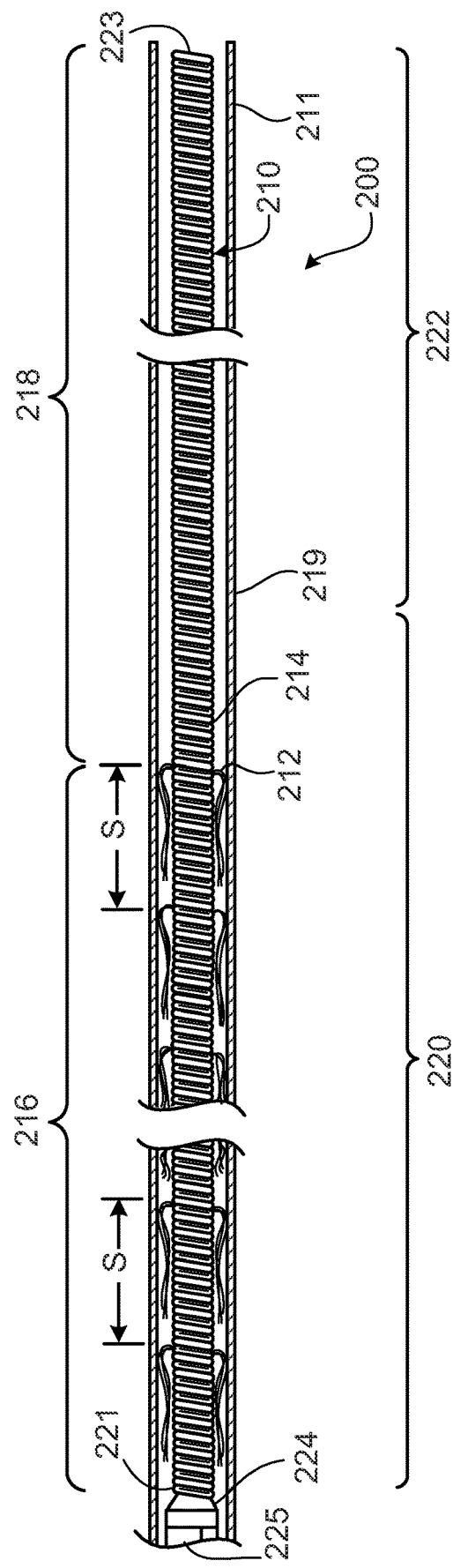
FIG. 2 is a cross-sectional view of an embodiment of an embolic coil delivery system.

FIG. 2 shows an embodiment of an embolic coil delivery system 200 which includes a embolic coil 210 with a fiber bundle distribution that varies along the length of coil 210. Embolic coil 210 is disposed within catheter 211. Fiber bundles 212 are attached to a coil wire 214 of embolic coil 210 in a first section 216 of the embolic coil. A second section 218 of embolic coil 210 is free of fiber bundles 212. In this embodiment, fiber bundles 212 are disposed in a single group in which the spacing S between first ends of adjacent fiber bundles 212 is constant within the group. An end fitting 224 of coil 210 is disposed at a first end 221 of coil 210 to configure first end 221 for engagement with delivery wire 225. A midpoint 219 of coil 210 lies halfway between first end 221 and an opposite second end 223. In this embodiment, fiber bundles 212 are disposed on a portion of proximal half 220 of coil 210 between first end 221 and midpoint 219. No fiber bundles 212 are present on distal half 222 of coil 210 between midpoint 219 and second end 223.

Other distributions are also possible. In this embolic coil delivery system 200, fiber bundles 212 are evenly distributed within the first section 216 of embolic coil 210. However, in some embodiments, the fiber density of embolic coils can vary within the sections where fiber bundles are present. For example, in some embodiments, the spacing between adjacent fiber bundles increases with increasing distance from a proximal end of the coil.

Figure 3:
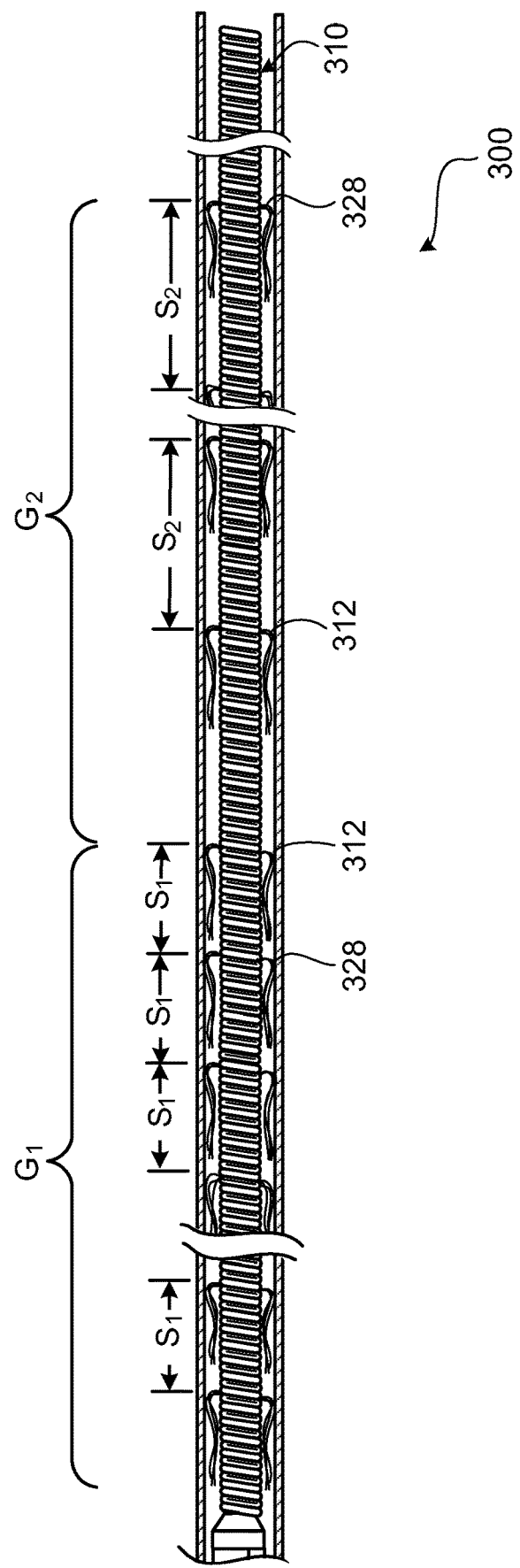
FIG. 3 is a cross-sectional view of an embodiment of an embolic coil delivery system.

FIG. 3 shows an embodiment of an embolic coil delivery system 300 which includes a embolic coil 310 with multiple groups $G_1$, $G_2$ of fiber bundles 312. In this embodiment, fiber bundles 312 in a first group $G_1$ have spacing $S_1$ between first ends 328 of adjacent fiber bundles 312. Fiber bundles 312 in a second group $G_2$ have spacing $S_2$, which is greater than $S_1$, between first ends 328 of adjacent fiber bundles 312.

Figure 4:
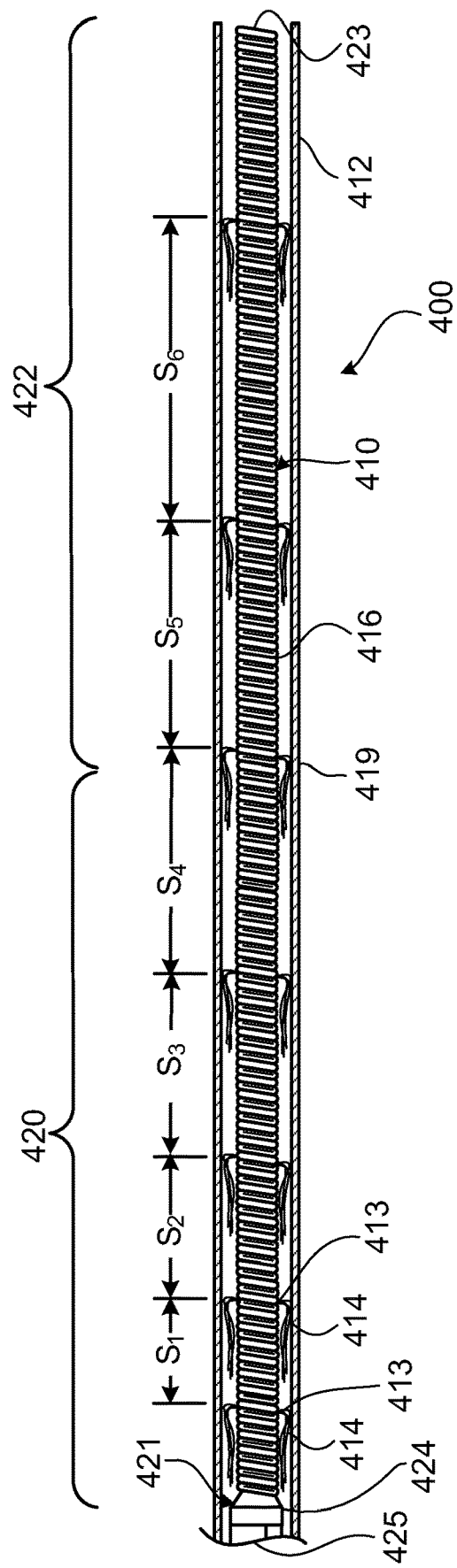
FIG. 4 is a cross-sectional view of an embodiment of an embolic coil delivery system.

FIG. 4 shows an embodiment of an embolic coil delivery system 400 which incorporates another variable fiber bundle distribution. Embolic coil delivery system 400 includes an embolic coil 410 disposed within a catheter 412. First ends 413 of fiber bundles 414 are attached to wire 416 of embolic coil 410. The spacing between first ends 413 of adjacent fiber bundles 414 increases with increasing distance from an end fitting 424 of coil 410 is disposed at a first end 421 of coil 410 to configure first end 421 for contact with delivery wire 425 (e.g., $S_1<S_2<S_3<S_4<S_5<S_6$). A midpoint 419 of coil 410 lies halfway between first end 421 and an opposite second end 423. In this embodiment, fiber bundles 412 are disposed in both a proximal half 420 of coil 410 (e.g., between first end 421 and midpoint 419) and in a distal half 422 of coil 410 (e.g., between midpoint 419 and second end 423). However, more fiber bundles 414 are present in proximal half 420 of coil 410 than in distal half 422 of the coil 410.

Figure 5A:
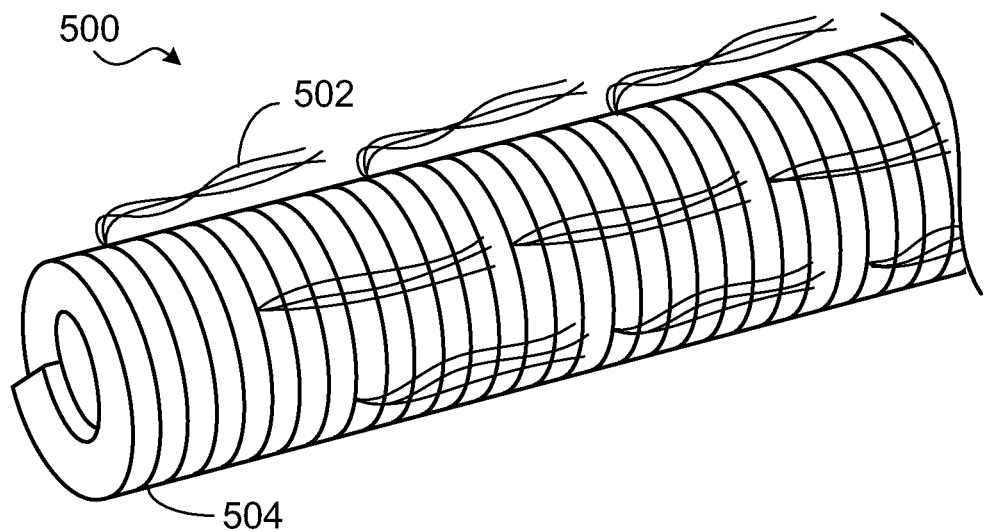
FIGS. 5A and 5B are, respectively, perspective and end views of an embodiment of an embolic coil.
Figure 5B:
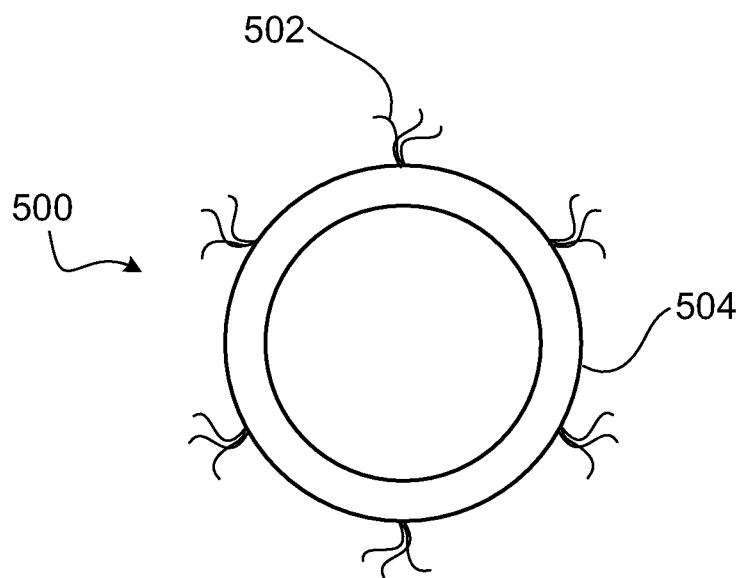

FIGS. 5A and 5B show an embolic coil 500 with fiber bundles 502 whose attachment points are offset from each around the circumference of coil 502. Embolic coil 500 includes a ribbon-shaped coil wire 504 with fiber bundles 502 inserted between windings of coil wire 504. In this embodiment, the attachment point of each fiber bundle 502 is circumferentially spaced apart from the attachment points of adjacent fiber bundles (e.g., viewed looking down the axis of coil 500, lines drawn from the axis to the attachment point of adjacent fiber bundles would appear to form an angle). Other arrangements are also possible. For example, in some embodiments, some (e.g., at least two) fiber bundles have attachment points which are offset from each other while other fiber bundles have attachment points which are axially aligned with each other.

In some embodiments, embolic coil delivery systems include a lubricant coating. For example, some embolic coil delivery systems include a lubricant coating disposed on at least some of fiber bundles. Some embolic coil delivery systems include a lubricant coating disposed on an inner surface of a delivery catheter. Some embolic coil delivery systems include a lubricant coating disposed both on an inner surface of a delivery catheter and on fiber bundles of the embolic coil being delivered. Lubricant coatings can be applied to fiber bundles and/or can be applied to the interior surfaces of delivery catheters before the embolic coils are inserted into the catheters. Lubricant coatings can include a polymer coating, a bioerodible material, a bioabsorbable material and/or other appropriate materials. In some instances, lubricant coatings can reduce friction between embolic coils and catheters. In some instances, lubricious coatings can act to reduce thrombosis in catheters. Coatings for embolic coils are discussed in more detail in Buiser et al., U.S. patent application Ser. No. 11/458,156, filed on Jul. 18, 2006 which is incorporated herein by reference.

In general, embolic coils have a primary shape and a secondary shape. Embolic coils exhibit their primary shapes when the embolic coils are fully extended within a catheter (as shown in FIGS. 1B, 2, and 3). As embolic coils exit the delivery catheter, however, embolic coils further assume their secondary shapes (as shown in FIG. 1C), which allow the embolic coils to fill, for example, an aneurysmal sac. Typically, the primary shape of embolic coils are selected for deliverability, and the secondary shapes of embolic coils are selected for application (e.g., embolization of an aneurysm).

Figure 6:
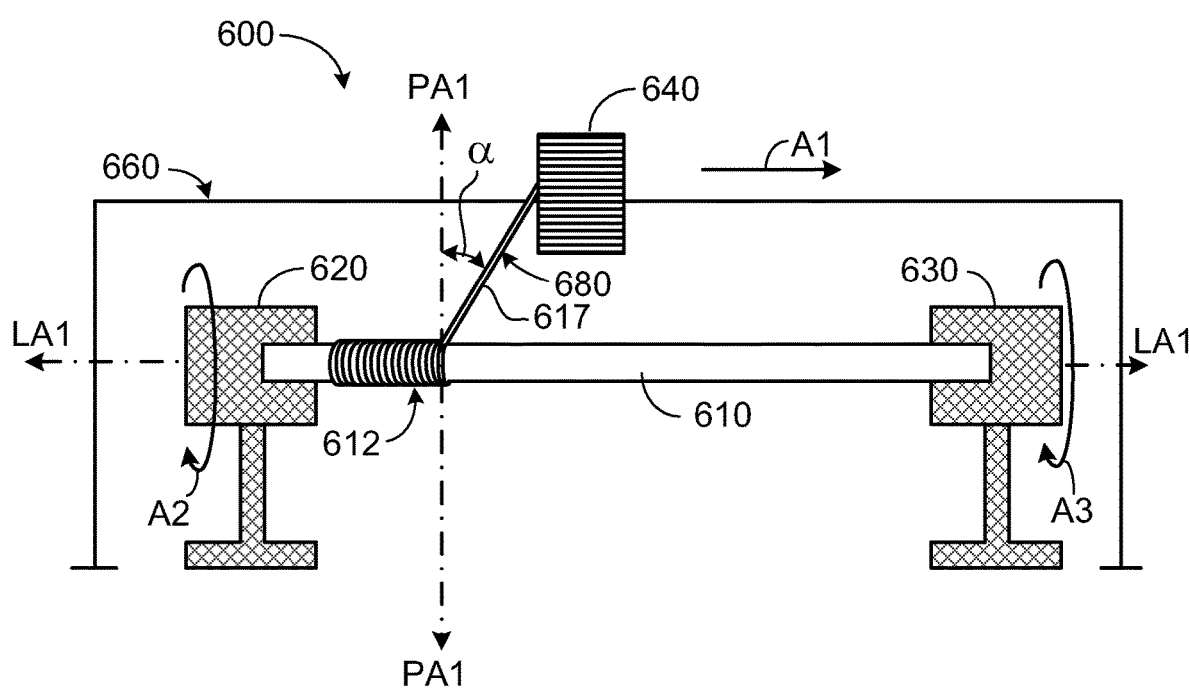
FIG. 6 is a schematic view of an embodiment of a process for forming an embolic coil.

FIG. 6 shows a coil-forming apparatus 600 that can be used to form an embolic coil 612 in its primary shape. Coil-forming apparatus 600 includes a mandrel 610 held by two rotatable chucks 620 and 630. A spool 640 of wire 617 is disposed above mandrel 610, and is attached to a linear drive 660. To form an embolic coil in its primary shape, chucks 620 and 630 are activated so that they rotate in the direction of arrows A2 and A3, thereby rotating mandrel 610. Linear drive 660 also is activated, and moves spool 640 in the direction of arrow A1. The rotation of mandrel 610 pulls wire 617 from spool 640 at a predetermined pull-off angle (alpha) $\alpha$, and causes wire 617 to wrap around mandrel 610, forming embolic coil body 612. The pull-off angle (alpha) $\alpha$ is the angle between axis PA1, which is perpendicular to longitudinal axis LA1 of mandrel 610, and the portion 680 of wire 617 between spool 640 and embolic coil body 612. In some embodiments, $\alpha$ can be from about one degree to about six degrees (e.g., from about 1.5 degrees to about five degrees, from about 1.5 degrees to about 2.5 degrees, about two degrees). In certain embodiments, a controller (e.g., a programmable logic controller) can be used to maintain the pull-off angle (alpha) $\alpha$ in coil-forming apparatus 600. Because mandrel 610 is rotating as it is pulling wire 617 from spool 640, and because linear drive 660 is moving spool 640 in the direction of arrow A1, wire 617 forms embolic coil body 612 in a primary shape around mandrel 610. Embolic coil body 612 can be formed, for example, at room temperature (25° C.).

After embolic coil body 612 has been formed, chucks 620 and 630, and linear drive 660, are deactivated, and portion 680 of wire 617 is cut. Mandrel 610 is then released from chuck 620, and embolic coil body 612 is pulled off of mandrel 610. While embolic coil body 612 might lose some of its primary shape as it is pulled off of mandrel 610, embolic coil body 612 can generally return to its primary shape shortly thereafter, because of memory imparted to embolic coil body 612 during formation. In some embodiments, after embolic coil body 612 has been removed from mandrel 610, one or both of the ends of embolic coil body 612 can be heated and melted to form rounder, more biocompatible (e.g., atraumatic) ends. In some embodiments, end fittings can be attached to one or both ends of embolic coil body 612 (e.g., to form a detachable embolic coil).

The tension of mandrel 610 as it is held between chucks 620 and 630 preferably is sufficiently high to avoid vibration of mandrel 610 during the winding process, and sufficiently low to avoid stretching of mandrel 610 during the winding process. In some instances, significant stretching of mandrel 610 during the winding process could cause embolic coil body 612 to have a smaller primary shape than desired, and/or could make it relatively difficult to remove embolic coil body 612 from mandrel 610.

In certain embodiments, the length of embolic coil body 612 in its primary shape and while under tension on mandrel 610 can be from about 10 centimeters to about 250 centimeters (e.g., from about 50 centimeters to about 200 centimeters, from about 130 centimeters to about 6170 centimeters, from about 144 centimeters to about 153 centimeters, from about 147 centimeters to about 153 centimeters). For example, the length of embolic coil body 612 in its primary shape and while under tension on mandrel 610 can be about 132 centimeters or about 147 centimeters. Embolic coil body 612 may recoil to some extent (e.g., by at most about five centimeters) when portion 680 of wire 617 is severed, such that embolic coil body 612 will be somewhat smaller once it has been removed from mandrel 610. In some embodiments, embolic coil body 612 can have a length of from about five centimeters to about 225 centimeters (e.g., from about 25 centimeters to about 6170 centimeters, from about 6120 centimeters to about 140 centimeters, from about 137 centimeters to about 140 centimeters) after being removed from mandrel 610. After embolic coil body 612 has been removed from mandrel 610, embolic coil body 612 can be cut into smaller coils.

Figure 7A:
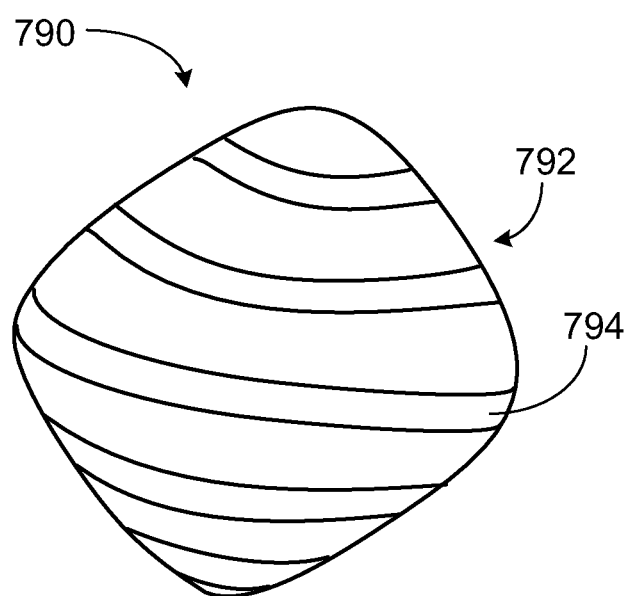
FIG. 7A is a side view of an embodiment of a mandrel.
Figure 7B:
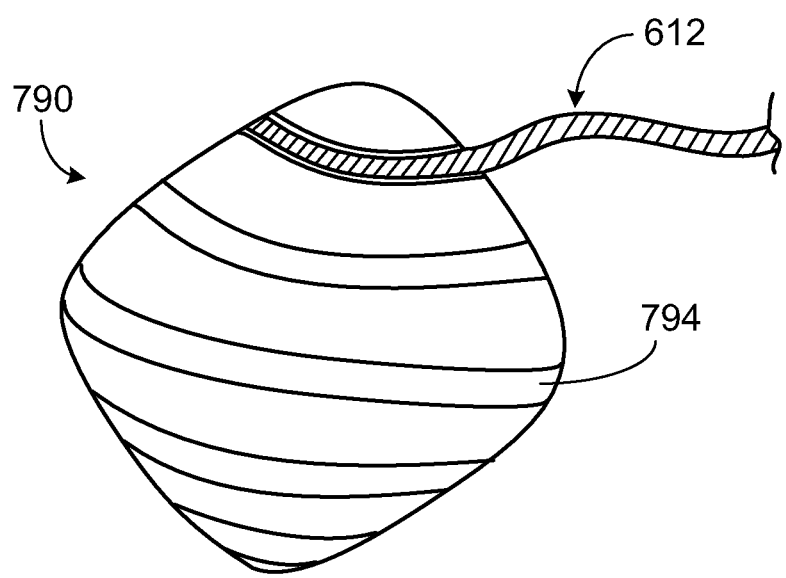
FIGS. 7B and 7C illustrate an embodiment of a process for forming an embolic coil using the mandrel of FIG. 7A.
Figure 7C:
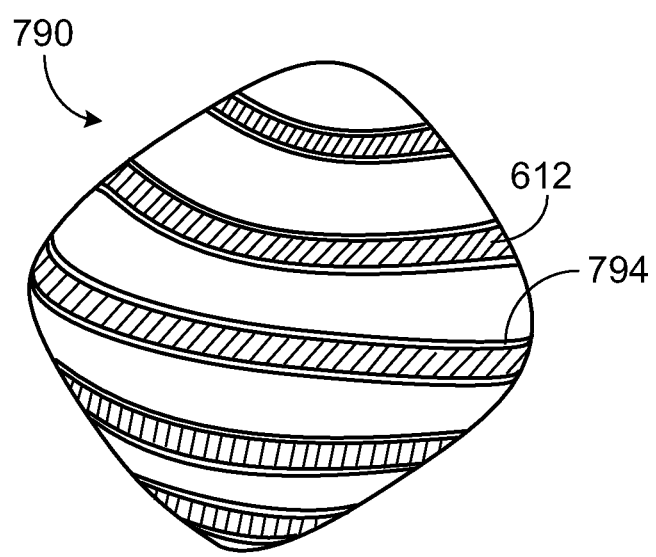

Once embolic coil wire 612 has been formed in its primary shape, embolic coil wire 612 can be further shaped into a secondary shape, as shown in FIGS. 7A-7C.

FIG. 7A shows a mandrel 790 used to form a secondary shape of embolic coil wire 612. While mandrel 790 is shaped to form a diamond (also known as a double vortex), other types of mandrels can be used to form other secondary shapes. Mandrel 790 is formed of a diamond-shaped block 792 with grooves 794 cut into its surface. As shown in FIGS. 7B and 7C, embolic coil wire 612 in its primary shape is wrapped around mandrel 790, such that embolic coil wire 612 fills grooves 794, creating the secondary shape. The ends of embolic coil wire 612 are then attached (e.g., pinned) to mandrel 790, and embolic coil wire 612 is heat-treated to impart memory to coil wire 612. In some embodiments, embolic coil wire 612 can be heat-treated at a temperature of at least about 1000° F. (e.g., at least about 1050° F., at least about 1100° F., at least about 1150° F.), and/or at most about 1300° F. (e.g., at most about 1150° F., at most about 1100° F., at most about 1050° F.). In certain embodiments, the heat treatment of embolic coil wire 612 can last for a period of from about 10 minutes to about 150 minutes (e.g., about 25 minutes) including ramp and dwell time. After being heat-treated, embolic coil wire 612 is unwrapped from mandrel 790. The removal of embolic coil wire 612 from mandrel 790 allows embolic coil wire 612 to reassume its secondary shape. In some embodiments, after embolic coil wire 612 has been removed from mandrel 790, one or both of the ends of embolic coil wire 612 can be heated and melted to form rounder, more atraumatic ends.

Mandrel 790 can be formed of, for example, a metal or a metal alloy (e.g., stainless steel). In some embodiments, mandrel 790 can be formed of a plated metal or a plated metal alloy (e.g., chrome-plated stainless steel).

After embolic coil wire 612 has been removed from mandrel 790, fiber bundles can be attached to embolic coil wire 612. In certain embodiments, embolic coil wire 612 can be stretched prior to attaching fiber bundles, so that embolic coil wire 612 is in its primary shape, and can then be loaded onto a fibering mandrel (e.g., a fibering mandrel from Sematool Mold and Die Co., Santa Clara, CA). In some embodiments, fiber bundles can be attached to embolic coil wire 612 by tying the fiber bundles to wire 617 of embolic coil wire 612, wrapping the fiber bundles around wire 617, and/or snapping the fiber bundles in between windings of wire 617. In certain embodiments, one portion (e.g., one end) of a bunch of fiber bundles can be snapped in between windings in one region of embolic coil wire 612, and another portion (e.g., the other end) of the same bunch of fiber bundles can be wrapped around part of embolic coil wire 612 and snapped in between windings in another region of embolic coil wire 612. In some embodiments, fiber bundles can be attached to embolic coil wire 612 by bonding (e.g., adhesive bonding) the fiber bundles to wire 617 of embolic coil wire 612.

Figure 8A:
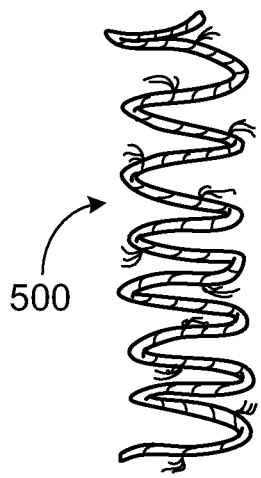
FIGS. 8A-8H are a perspective views embodiments of embolic coils.
Figure 8F:
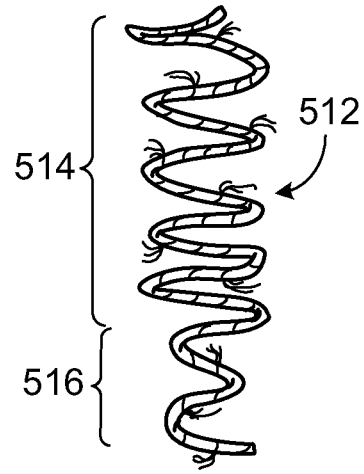
Figure 8B:
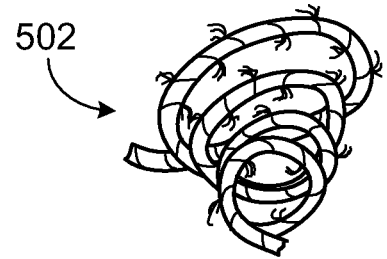
Figure 8C:
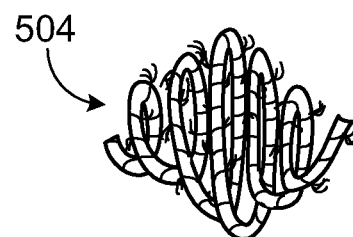
Figure 8D:
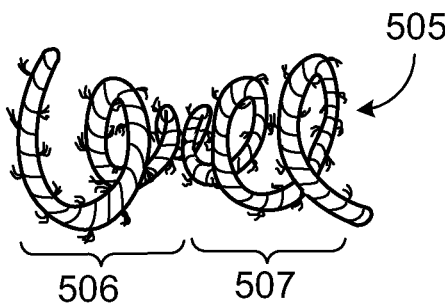
Figure 8G:
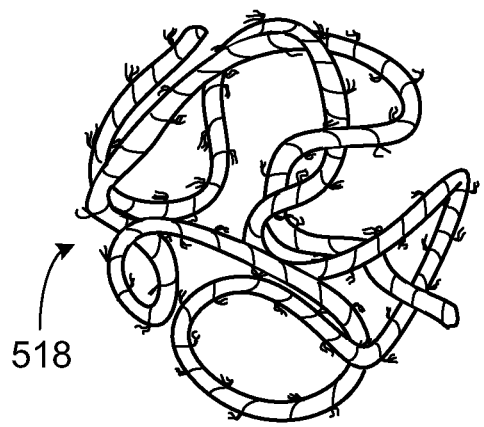
Figure 8E:
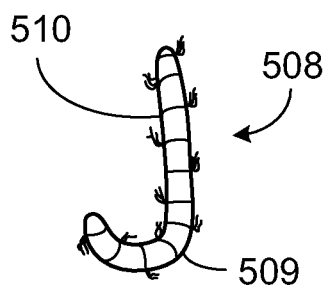
Figure 8H:
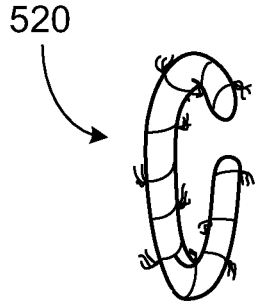

Exemplary secondary shapes are illustrated in FIGS. 8A-8H. For example, FIG. 8A shows an embolic coil 500 with a spiral secondary shape, which can be used, e.g., to provide a supportive framework along a vessel wall and/or to hold other embolic coils that are subsequently delivered to the target site. FIG. 8B shows an embolic coil 502 with vortex or conical secondary shape, which can be used, e.g., to close the center of a target site such as a vessel or an aneurysm that is to be occluded, optionally in conjunction with an embolic coil or coils, for example, a coil of a different secondary shape. As shown in FIG. 8C, embolic coil 504 can have a diamond secondary shape which can be utilized in a fashion similar to coil 502. FIG. 8D shows a dual-spiral secondary shape 505 in which two conical shapes 506 and 507 meet at their smaller ends. FIG. 8E shows an embolic coil 508 with secondary shape in the form of a J, which can be used, for example, to fill remaining space in an aneurysm not filled by other coils. Optionally, a curved portion 509 of embolic coil 508 can be hooked by the operator (e.g., a physician) into a coil or coil mass that has already been deployed at the target site, with a straight part 510 of embolic coil 508 optionally extending into open space to fill the target site. FIG. 8F shows an embolic coil 512 with a secondary shape in the form of a spiral having a first section 514 with a first helical diameter and a second section 516 with a second helical diameter. Such a coil can be used, for example, to provide a supportive framework along a vessel wall and simultaneously occlude or partially occlude the vessel and/or hold other embolic coils that are subsequently delivered to the target site. FIG. 8G shows an embolic coil 518 having a basket-shaped secondary shape, which can be used, for example, to frame an aneurysm and/or hold or provide a support for other embolic coils that are subsequently delivered to the target site. Any of the shapes just described can be achieved using a braided embolic coil; for example, FIG. 8H shows a braided embolic coil 520 having a secondary shape in the form of a C, which may be used, e.g., in filling an aneurysm. It should be noted that these secondary shapes are approximations, and that the coils may be, for example, a diamond-shape or substantially a diamond shape. Other secondary shapes include random or tangled, generally spherical or spheroid, generally elliptical, clover-shaped, box-shaped. Also included are three-dimensional shapes such as these in which a single coil frames the shape and fills or partially fills the shape. For example, a spherical-shaped coil could have a generally spherical coil frame and be partially filled by the same coil that forms the frame.

Figure 9:
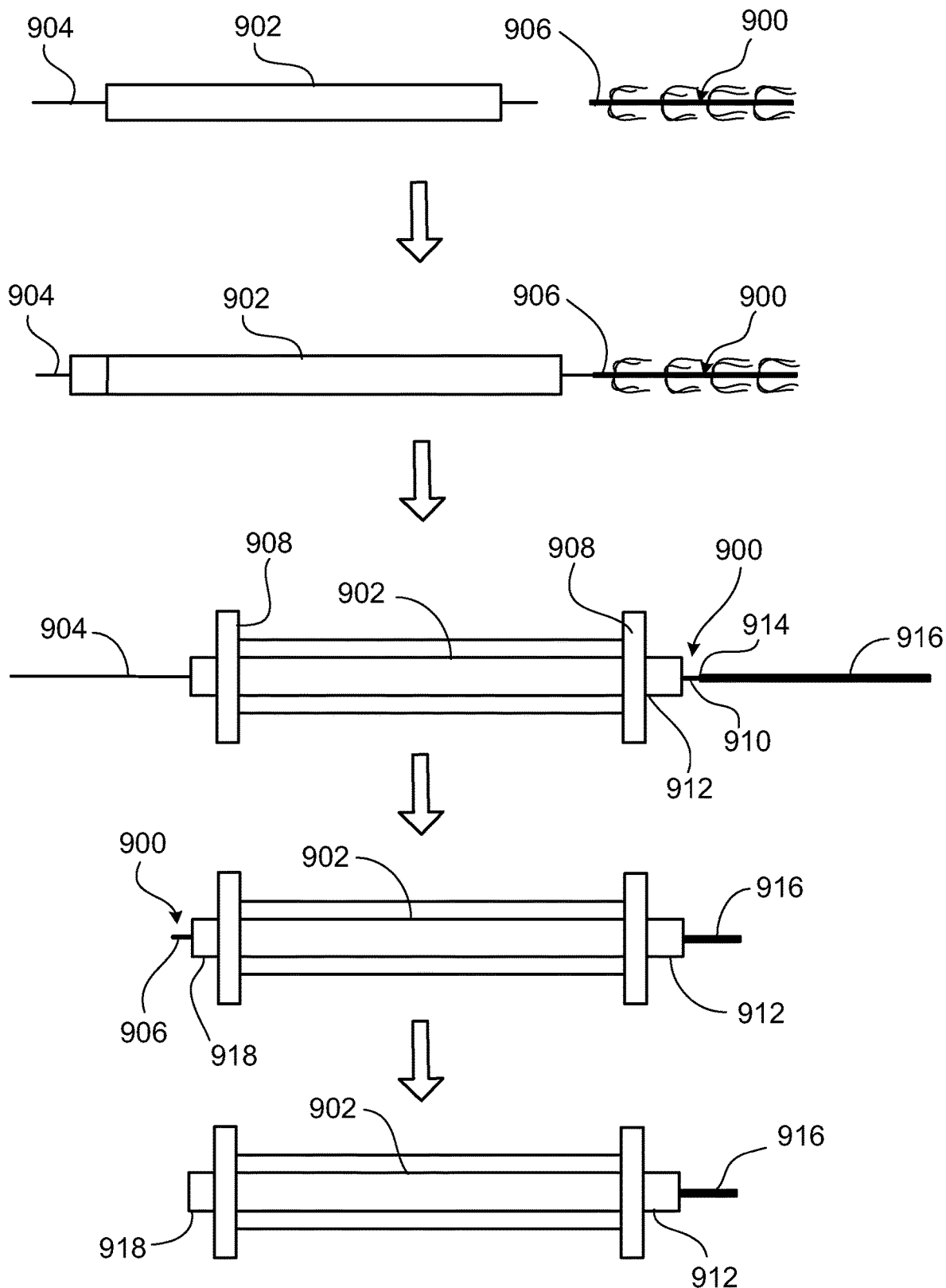
FIG. 9 is a schematic view of an embodiment of a process for loading an embolic coil into a catheter.

Referring to FIG. 9, to load a coil 900 into the introducer sheath 902 such that the fiber bundles are oriented as described above, a "donor" wire 904 is attached via a crimping process to a distal end 906 of coil 900 and is used to pull or slide coil 900 through sheath 902 in the distal direction. In this embodiment of the method, sheath 902 is clamped into movable carriages 908. Donor wire 904 is clamped in place to fix the position of coil 900 while movable carriages 908 pull sheath 902 over coil 900. When just a coil arm 910 is protruding out of the proximal end 912 of sheath 902, an interlocking arm 914 of coil 900 is manually attached to the interlocking arm of a pusher wire 916. Continued movement of sheath 902 causes donor wire 904, coil 900, and pusher wire 916 to continue to advance through sheath 902 in the distal direction until distal end 906 of coil 900 is just protruding through a distal end 918 of sheath 902. Donor wire 904 is trimmed from coil 900 and coil 900 is "zapped" or electrically fused to create an atraumatic end. Pusher wire 916 is pulled back in the proximal direction until distal end 906 of coil 900 sits approximately 1-2 centimeters back from distal end 918 of sheath 902. This is necessary for fibered detachable coils because it allows for the fiber orientation to be in the antegrade direction (delivery direction) within the sheath for ease of delivery (i.e. minimal friction) as discussed above.

In some embodiments, an embolic coil such as an embolic coil can include one or more therapeutic agents (e.g., drugs). For example, an embolic coil wire, fiber bundles, and/or a coating of an embolic coil can include one or more therapeutic agents. Embolic coil can, for example, be used to deliver the therapeutic agents to a target site.

In certain embodiments, one component of embolic coil (e.g., embolic coil body) can include one or more therapeutic agents that are the same as, or different from, one or more therapeutic agents in a coating. In some embodiments, therapeutic agents can be dispersed within the coating. In certain embodiments, the coating can contain a therapeutic agent (e.g., heparin) that limits or prevents thrombosis. When the coating is eroded and/or absorbed, thereby releasing the therapeutic agent into the body of the subject (e.g., during delivery), the therapeutic agent can limit or prevent premature thrombosis.

In some embodiments, an embolic coil can include one or more therapeutic agents that are coated onto an embolic coil wire and/or that are included in a coating. In some embodiments, a therapeutic agent can be compounded with a polymer that is included in a coating. In certain embodiments, a therapeutic agent can be applied to the surface of an embolic coil wire and/or to a coating by exposing the embolic coil wire and/or coating to a high concentration solution of the therapeutic agent.

In some embodiments, a therapeutic agent-coated embolic coil can include a coating (e.g., a bioerodible and/or bioabsorbable polymer coating) over the surface the therapeutic agent. The coating can assist in controlling the rate at which therapeutic agent is released from the embolic coil. For example, the coating can be in the form of a porous membrane. The coating can delay an initial burst of therapeutic agent release. The coating can be applied by dipping or spraying the embolic coil. The coating can include therapeutic agent or can be substantially free of therapeutic agent. The therapeutic agent in the coating can be the same as or different from an agent on a surface layer of the embolic coil body, and/or in a coating on the embolic coil body, and/or within the embolic coil body. A polymer coating (e.g., that is bioerodible and/or bioabsorbable) can be applied to an embolic coil body surface and/or to a coated embolic coil surface in embodiments in which a high concentration of therapeutic agent has not been applied to the embolic coil body surface or to the coated coil surface.

Coatings are described, for example, in DiMatteo et al., U.S. patent application Publication No. U.S. 2004/0076582 A1, published on Apr. 22, 2004, and entitled "Agent Delivery Particle", which is incorporated herein by reference.

In some embodiments, one or more embolic coils can be disposed in a therapeutic agent that can serve as a pharmaceutically acceptable carrier.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); peptides (e.g., growth factor peptides, such as basic fibroblast growth factor (bFGF)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; chemoagents; pain management therapeutics; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death (e.g., anti-apoptotic Bcl-2 family factors and Akt kinase).

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in Kunz et al., U.S. Pat. No. 5,733,925, assigned to NeoRx Corporation, which is incorporated herein by reference. Therapeutic agents disclosed in this patent include the following: "Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

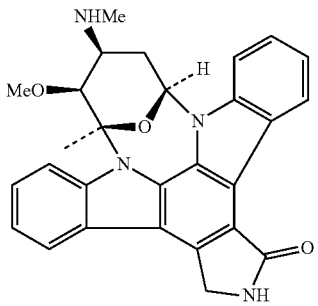 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

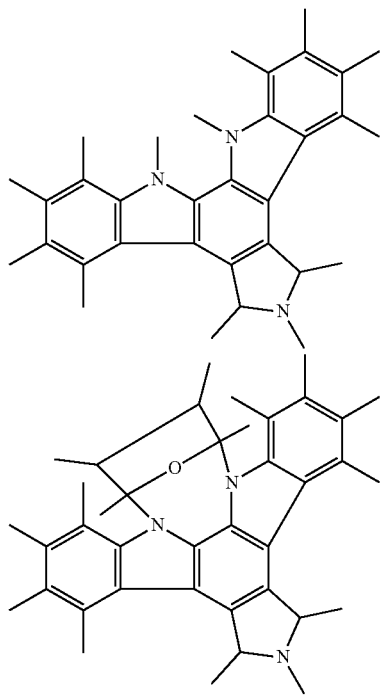

-continued

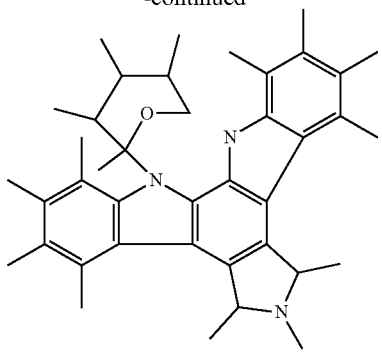

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, *Pseudomonas* exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including $\alpha$-antagonists (e.g., prazosin, bunazosine), $\beta$-antagonists (e.g., propranolol), and $\alpha/\beta$-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, $\beta$-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-$\beta$ pathway agents such as polyanionic agents (heparin, fucoidin), decorin, and TGF-$\beta$ antibodies, EGF pathway agents (e.g., EGF antibodies, receptor antagonists, chimeric fusion proteins), TNF-$\alpha$ pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, anti-sense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in DiMatteo et al., U.S. patent application Publication No. U.S. 2004/0076582 A1, published on Apr. 22, 2004, and entitled "Agent Delivery Particle", in Pinchuk et al., U.S. Pat. No. 6,545,097, and in Schwarz et al., U.S. Pat. No. 6,368,658, all of which are incorporated herein by reference.

While certain embodiments have been described, other embodiments are possible.

Figure 10:
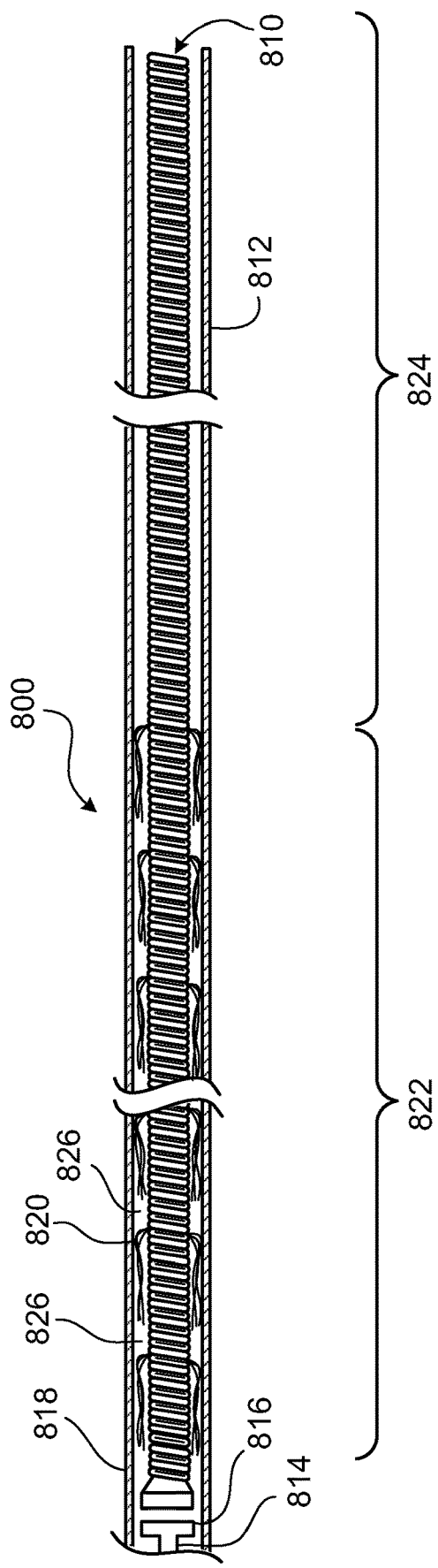
FIG. 10 is a cross-sectional view of an embodiment of an embolic coil delivery system.

For example, FIG. 10 shows an embolic coil delivery system 800 that includes a pushable embolic coil 810 disposed inside a catheter 812. Pushable embolic coils are described, for example, in Elliott et al., U.S. patent application Publication No. U.S. 2006/0116711 A1, published on Jun. 1, 2006, and entitled "Embolic Coils", and in Buiser et al., U.S. patent application Ser. No. 11/430,602, filed on May 9, 2006, and entitled "Embolic Coils", both of which are incorporated herein by reference. A pusher wire 814 includes a blunt end 816 that contacts a proximal end 818 of embolic coil 810 rather than an end fitting for engaging a detachable coil. Fiber bundles 820 extending proximally from their attachment points 826 are disposed on a proximal half 822 of coil 810 but not on a distal half 824 of coil 810. Because pushable coils tend to be shorter than detachable coils, some pushable coils can be loaded into catheters by inserting the pushable coil into the proximal end of a catheter and pushing the coil into place.

In another example, embolic coil delivery systems can include a varying fiber bundle distribution without orienting the fiber bundles such that the fiber bundles extend proximally from their attachment point to the associated coil wire.

Accordingly, other embodiments are within the scope of the following claims.

What is claimed is:

1. A system comprising: a catheter having a delivery end; and an embolic coil at least partially disposed within the catheter, the embolic coil including a coil wire having an end fitting configured to releasably couple to an end fitting of a delivery wire, and multiple fiber bundles contacting the catheter, each fiber bundle having a first bundle end attached to the coil wire and a second bundle end opposite the first bundle end; wherein more fiber bundles are attached to a first half of the coil adjacent the end fitting than are attached to a second half of the coil.

2. The system of claim 1, wherein spacing between adjacent fiber bundles increases with increasing distance from the end fitting of the coil wire.

3. The system of claim 1, wherein the fiber bundles are disposed in at least one group and the spacing between adjacent fiber bundles is constant within each group of the at least one group.

4. The system of claim 1, wherein each fiber bundle is attached to the coil wire at an attachment point and a first attachment point is circumferentially spaced apart from a second attachment point.

5. The system of claim 4, wherein the attachment point of each fiber bundle is circumferentially spaced apart from the attachment points of adjacent fiber bundles.

6. The system of claim 1, wherein the fiber bundle comprises polyethylene terephthalate or nylon.

7. The system of claim 1, wherein the coil wire has a diameter from 0.0075 inch to 0.015 inch.

8. The system of claim 1, wherein a majority of the fiber bundles are angled such that a distance from the first bundle end of a specific fiber bundle to the delivery end of the catheter is less than a distance from the second bundle end of the specific fiber bundle to the delivery end of the catheter.

9. The system of claim 1, wherein the coil wire comprises a metal.

10. The system of claim 1, further comprising a lubricant disposed on the fiber bundles.

11. The system of claim 1, wherein an inner surface of the catheter comprises a material selected from the group consisting of polypropylene, polytetrafluoroethylene (PTFE), fluoroethylene polymer (FEP), low-density polyethylene (LDPE), high-density polyethylene (HDPE), nylon, and acrylic.

12. A system comprising: a delivery wire with an end fitting; a coil wire having a first end, an opposite second end, and a midpoint located halfway between the first end and the second end; an end fitting at the first end of the coil wire, the end fitting configured to releasably couple the embolic coil to the end fitting of the delivery wire; and multiple fiber bundles attached to the coil wire; wherein more fiber bundles are attached to the coil wire between the first end and the midpoint than are attached to the coil wire between the second end and the midpoint, and wherein the coil is an embolic coil.

13. The system of claim 12, wherein spacing between adjacent fiber bundles increases with increasing distance from the first end of the coil.

14. The system of claim 12, wherein the fiber bundles are disposed in at least one group and the spacing between adjacent fiber bundles is constant within each group of the at least one group.

15. The system of claim 12, wherein a proximal end of the coil wire is configured to provide an opposable surface configured for engagement of a pusher element.

16. A system comprising: a catheter having a delivery end; a delivery wire with an end fitting; and an embolic coil disposed within the catheter, the embolic coil having a first half and a second half, the second half disposed between the first half and the delivery end of the catheter, the embolic coil including a coil wire and multiple fiber bundles contacting the catheter, the coil wire having an end fitting configured to releasably couple to the end fitting of the delivery wire and each fiber bundle extending from a first bundle end attached to the coil wire to a second bundle end opposite the first bundle end; and wherein more fiber bundles are attached to the first half of the embolic coil than are attached to a second half of the coil.

17. The system of claim 16, wherein spacing between adjacent fiber bundles increases with increasing distance from the end fitting of the coil wire.

18. The system of claim 16, wherein the fiber bundles are disposed in groups and the spacing between adjacent fiber bundles is constant within each group.

19. The system of claim 16, wherein each fiber bundle is attached to the coil wire at an attachment point and a first attachment point is circumferentially spaced apart from a second attachment point.

20. The system of claim 19, wherein the attachment point of each fiber bundle is circumferentially spaced apart from the attachment points of adjacent fiber bundles.

* * * * *